United States Patent
Hamrah et al.

(10) Patent No.: US 11,007,076 B1
(45) Date of Patent: May 18, 2021

(54) BRUXISM MOUTH GUARD DEVICE AND SYSTEM INCLUDING THE SAME

(71) Applicants: Sanaz Daneshfar Hamrah, Vienna, VA (US); Kenny Kambiz Broukhim, West Hills, CA (US)

(72) Inventors: Sanaz Daneshfar Hamrah, Vienna, VA (US); Kenny Kambiz Broukhim, West Hills, CA (US)

(*) Notice: Subject to any disclaimer, the term of this patent is extended or adjusted under 35 U.S.C. 154(b) by 385 days.

(21) Appl. No.: 15/913,493

(22) Filed: Mar. 6, 2018

Related U.S. Application Data (60) Provisional application No. 62/517,956, filed on Jun. 11, 2017.

(51) Int. Cl.
*A61C 5/14* (2006.01)
*A61F 5/56* (2006.01)
*A61B 5/00* (2006.01)

(52) U.S. Cl.
CPC ............ *A61F 5/566* (2013.01); *A61B 5/4557* (2013.01); *A61B 5/486* (2013.01); *A61B 5/7455* (2013.01); *A61F 2005/563* (2013.01)

(58) Field of Classification Search
CPC ...... A61F 5/56; A61F 2005/563; A61F 5/566; A61F 5/00; A61B 5/4551; A61B 5/486; A61B 5/7455; A61B 5/4557; A61C 7/008; A61C 7/08
USPC ................ 128/861, 854, 848; 601/46; 433/6
See application file for complete search history.

(56) References Cited

U.S. PATENT DOCUMENTS

| | | | |
|---|---|---|---|
| 4,838,283 | A | 6/1989 | Lee, Jr. |
| 4,979,516 | A | 12/1990 | Abraham, II |
| 5,078,153 | A | 1/1992 | Nordlander et al. |
| 5,190,051 | A | 3/1993 | Wilson |

(Continued)

FOREIGN PATENT DOCUMENTS

WO 2008/061328 A2 5/2008

OTHER PUBLICATIONS

Pro Form NiteGuard—Full Review, Mouth Guards For Teeth Grinding Website, Web page <http://mouthguardsforteethgrinding.com:80/pro-form-niteguard-review/>, 7 pages, dated Mar. 16, 2016, retrieved from Internet Archive Wayback Machine <https://web.archive.org/web/20160316051834/http://mouthguardsforteethgrinding.com:80/pro-form-niteguard-review/> on Oct. 8, 2018.

(Continued)

*Primary Examiner* — Victoria J Hicks
(74) *Attorney, Agent, or Firm* — The Law Office of Patrick F. O'Reilly III, LLC

(57) ABSTRACT

A bruxism mouth guard device is disclosed herein. The bruxism mouth guard device includes a mouth guard body portion with a channel formed therein for receiving one or more teeth of a user; one or more pressure sensing devices for sensing a grinding or clenching of the one or more teeth of the user; a vibration device for vibrating one or more portions of the mouth of the user; and a control device operatively coupled to the one or more pressure sensing devices and the vibration device, the control device activating the vibration device so as to vibrate the one or more portions of the mouth of the user when the one or more pressure sensing devices sense the grinding or clenching of the one or more teeth by the user. A bruxism mouth guard system including the device is also disclosed herein.

10 Claims, 10 Drawing Sheets

(56) References Cited

U.S. PATENT DOCUMENTS

| | | | |
|---|---|---|---|
| 5,490,520 | A | 2/1996 | Schaefer et al. |
| 5,553,626 | A | 9/1996 | Burger et al. |
| 5,586,562 | A | 12/1996 | Matz |
| 6,089,864 | A * | 7/2000 | Buckner .................. A61F 5/56 433/6 |
| 6,270,466 | B1 | 8/2001 | Weinstein et al. |
| 8,961,437 | B2 | 2/2015 | Al-Tawil |
| 9,731,103 | B1 * | 8/2017 | Rouse .................. A61M 31/00 |
| 2009/0309747 | A1 * | 12/2009 | Ghovanloo ............. A61F 4/00 340/686.1 |
| 2011/0160618 | A1 | 6/2011 | Shemesh et al. |
| 2013/0171599 | A1 * | 7/2013 | Bleich .................. A61B 5/0456 434/247 |
| 2014/0072932 | A1 * | 3/2014 | Brawn .................. A61N 5/062 433/173 |
| 2015/0045705 | A1 * | 2/2015 | Baba .................. A61F 5/566 601/46 |
| 2015/0150501 | A1 | 6/2015 | George et al. |
| 2015/0297390 | A1 | 10/2015 | Schlatter et al. |
| 2015/0305671 | A1 * | 10/2015 | Yoon .................. A61B 5/681 600/301 |
| 2016/0095740 | A1 * | 4/2016 | Mardirossian .......... A61F 5/566 128/847 |
| 2016/0143770 | A1 * | 5/2016 | Vezina .................. A61F 5/566 128/861 |
| 2016/0242951 | A1 * | 8/2016 | Berk .................. A61B 5/7405 |

OTHER PUBLICATIONS

J&S Dental Lab Custom Night Guards—Full Review, Mouth Guards for Teeth Grinding Website, Web page <http://mouthguardsforteethgrinding.com:80/js-dental-lab-custom-night-guards-full-review/>, 12 pages, dated Mar. 16, 2016, retrieved from Internet Archive Wayback Machine <https://web.archive.org/web/20160316044933/http://mouthguardsforteethgrinding.com:80/js-dental-lab-custom-night-guards-full-review/> on Oct. 8, 2018.

SleepGuard Biofeedback Headband—Full Review, Mouth Guards for Teeth Grinding Website, Web page <http://mouthguardsforteethgrinding.com/biofeedback-headband/>, 14 pages, dated Apr. 1, 2016, retrieved from Internet Archive Wayback Machine <https://web.archive.org/web/20160401081511/http://mouthguardsforteethgrinding.com/biofeedback-headband/> on Oct. 8, 2018.

Rest Assured / Eliminator Pro Night Guard—Full Review, Mouth Guards for Teeth Grinding Website, Web page <http://mouthguardsforteethgrinding.com/rest-assured-review/>, 8 pages, dated Apr. 1, 2016, retrieved from Internet Archive Wayback Machine <http://web.archive.org/web/20160401081527/http://mouthguardsforteethgrinding.com/rest-assured-review/> on Oct. 8, 2018.

* cited by examiner

SECTION A-A

SECTION B-B

SECTION C-C

BRUXISM MOUTH GUARD DEVICE AND SYSTEM INCLUDING THE SAME

CROSS-REFERENCE TO RELATED APPLICATIONS

This patent application claims priority to, and incorporates by reference in its entirety, U.S. Provisional Patent Application No. 62/517,956, entitled "Bruxism Mouth Guard Device And System Including The Same", filed on Jun. 11, 2017.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a bruxism mouth guard device and a bruxism mouth guard system including the same. More particularly, the invention relates to a bruxism mouth guard device and a bruxism mouth guard system for preventing the grinding or clenching of teeth by a user thereof.

2. Background

Bruxism is a condition in which teeth are grinded, gnashed, or clenched. The teeth clenching happens unconsciously during the clay, but mostly at night (sleep bruxism). Sleep bruxism is considered a sleep-related movement disorder. People who clench or grind their teeth (brux) during sleep are more likely to have other sleep disorders, such as snoring and pauses in breathing (sleep apnea). In many cases, bruxism can be frequent and severe enough to lead to jaw disorders, headaches, damaged teeth, and other problems.

Signs and symptoms of bruxism may include any one or more of the following: (i) teeth grinding or clenching, which may be loud enough to awaken your sleep partner; (ii) teeth that are flattened, fractured, chipped, or loose; (iii) worn tooth enamel, exposing deeper layers of your tooth; (iv) increased tooth sensitivity; (v) jaw or face pain or soreness; (vi) Tired or tight jaw muscles; (vii) pain that feels like an earache, though it is actually not a problem with one's ear; (viii) dull headache originating in the temples; (ix) damage from chewing on the inside of your cheek; and (x) indentations on your tongue.

Frequently, individuals with night bruxism wake up in the mornings with chronic jaw pain and headaches, as a result of grinding and/or clenching their teeth during the night. Typically, the only treatment that doctors recommend for night bruxism is to wear a mouth guard while sleeping. Although, while a mouth guard may remove some pressure off the jaw of a person with night bruxism, it does not remedy the underlying causes of the disease. In addition, when a mouth guard is worn by an individual over a long period of time, the mouth guard can eventually result in the deterioration of teeth and damage to the gums.

Therefore, what is needed is a bruxism mouth guard device that is configured to prevent the grinding or clenching of teeth of a user by providing a tactile sensation in the mouth of the user when the grinding or clenching of teeth is sensed. Moreover, a bruxism mouth guard device is needed that is capable of continually alerting a user of teeth grinding or clenching during sleep so that the frequency of the teeth grinding or clenching may eventually decrease over time. Furthermore, there is a need for a bruxism mouth guard system, which includes the bruxism mouth guard device, that enables the mouth guard portion of the device to be easily cleaned after use, and allows the power source of the device to be easily recharged between uses of the device.

BRIEF SUMMARY OF EMBODIMENTS OF THE INVENTION

Accordingly, the present invention is directed to a bruxism mouth guard device and a bruxism mouth guard system including the same that substantially obviates one or more problems resulting from the limitations and deficiencies of the related art.

In accordance with one or more embodiments of the present invention, there is provided a bruxism mouth guard device that includes a mouth guard body portion, the mouth guard body portion comprising a channel formed therein that is configured to receive one or more teeth of a user; one or more pressure sensing devices in or on the mouth guard body portion, the one or more pressure sensing devices configured to sense a grinding or clenching of the one or more teeth of the user; a vibration device in or on the mouth guard body portion, the vibration device configured to vibrate one or more portions of the mouth of the user; and a control device operatively coupled to the one or more pressure sensing devices and the vibration device, the control device configured to activate the vibration device so as to vibrate the one or more portions of the mouth of the user when the one or more pressure sensing devices sense the grinding or clenching of the one or more teeth by the user in order to prevent the grinding or clenching of the one or more teeth by the user.

In a further embodiment of the present invention, the one or more pressure sensing devices and the vibration device are each part of a sensing and vibration assembly that is removable from the mouth guard body portion so as to enable the mouth guard body portion to be cleaned separately from the sensing and vibration assembly.

In yet a further embodiment, the sensing and vibration assembly further comprises a power source configured to provide power for the one or more pressure sensing devices, the vibration device, and the control device.

In still a further embodiment, the power source of the sensing and vibration assembly comprises one or more batteries.

In yet a further embodiment, the sensing and vibration assembly further comprises a central housing portion containing the vibration device, the control device, and the power source; and the sensing and vibration assembly additionally comprises a peripheral housing portion containing the one or more pressure sensing devices.

In still a further embodiment, the mouth guard body portion further comprises an aperture disposed in a sidewall thereof configured to accommodate a portion of the central housing portion passing therethrough.

In yet a further embodiment, the peripheral housing portion of the sensing and vibration assembly is configured to be interiorly disposed within the mouth guard body portion.

In still a further embodiment, the central housing portion of the sensing and vibration assembly is configured to extend between a tongue of the user and a roof of the mouth of the user such that the vibration device is capable of vibrating both the tongue of the user and the roof of the mouth of the user.

In yet a further embodiment, the one or more pressure sensing devices are in the form of one or more piezoelectric sensors configured to sense a compression force exerted thereon by the grinding or clenching of the one or more teeth by the user.

In still a further embodiment, the control device is in the form of a circuit board that is operatively coupled to the one or more pressure sensing devices and the vibration device, the circuit board configured to activate the vibration device so as to vibrate the one or more portions of the mouth of the user when the one or more pressure sensing devices sense the grinding or clenching of the one or more teeth above a predetermined threshold value.

In yet a further embodiment, the mouth guard body portion further comprises one or more recesses for receiving respective ones of the one or more pressure sensing devices of the bruxism mouth guard device.

In still a further embodiment, the bruxism mouth guard device further comprises one or more sensor cover members configured to be inserted into respective ones of the one or more recesses in the mouth guard body portion in order to cover one or more respective portions of the one or more pressure sensing devices.

In accordance with one or more other embodiments of the present invention, there is provided a bruxism mouth guard system that includes a bruxism mouth guard device configured to worn inside a mouth of a user and a recharging unit configured to recharge the power source of the bruxism mouth guard device. The bruxism mouth guard device includes a mouth guard body portion, the mouth guard body portion comprising a channel formed therein that is configured to receive one or more teeth of the user; one or more pressure sensing devices in or on the mouth guard body portion, the one or more pressure sensing devices configured to sense a grinding or clenching of the one or more teeth of the user; a vibration device in or on the mouth guard body portion, the vibration device configured to vibrate one or more portions of the mouth of the user; a control device operatively coupled to the one or more pressure sensing devices and the vibration device, the control device configured to activate the vibration device so as to vibrate the one or more portions of the mouth of the user when the one or more pressure sensing devices sense the grinding or clenching of the one or more teeth by the user in order to prevent the grinding or clenching of the one or more teeth by the user; and a power source configured to provide power for the one or more pressure sensing devices, the vibration device, and the control device.

In a further embodiment of the present invention, the one or more pressure sensing devices and the vibration device of the bruxism mouth guard device are each part of a sensing and vibration assembly that is removable from the mouth guard body portion so as to enable the mouth guard body portion to be cleaned separately from the sensing and vibration assembly.

In yet a further embodiment, the sensing and vibration assembly of the bruxism mouth guard device further comprises a central housing portion containing the vibration device, the control device, and the power source; and the sensing and vibration assembly additionally comprises a peripheral housing portion containing the one or more pressure sensing devices.

In still a further embodiment, the mouth guard body portion of the bruxism mouth guard device further comprises an aperture disposed in a sidewall thereof configured to accommodate a portion of the central housing portion passing therethrough.

In yet a further embodiment, the peripheral housing portion of the sensing and vibration assembly of the bruxism mouth guard device is configured to be interiorly disposed within the mouth guard body portion.

In still a further embodiment, the central housing portion of the sensing and vibration assembly of the bruxism mouth guard device is configured to extend between a tongue of the user and a roof of the mouth of the user such that the vibration device is capable of vibrating both the tongue of the user and the roof of the mouth of the user.

In yet a further embodiment, a bottom portion of the central housing portion of the sensing and vibration assembly of the bruxism mouth guard device is configured to be received within a recess on a top portion of the recharging unit.

In still a further embodiment, during the charging of the power source of the bruxism mouth guard device, the sensing and vibration assembly is configured to be disposed on the recharging unit without being attached to the mouth guard body portion.

In yet a further embodiment, the one or more pressure sensing devices of the bruxism mouth guard device are in the form of one or more piezoelectric sensors configured to sense a compression force exerted thereon by the grinding or clenching of the one or more teeth by the user.

In still a further embodiment, the control device of the bruxism mouth guard device is in the form of a circuit board that is operatively coupled to the one or more pressure sensing devices and the vibration device, the circuit board configured to activate the vibration device so as to vibrate the one or more portions of the mouth of the user when the one or more pressure sensing devices sense the grinding or clenching of the one or more teeth above a predetermined threshold value.

In yet a further embodiment, the mouth guard body portion of the bruxism mouth guard device further comprises one or more recesses for receiving respective ones of the one or more pressure sensing devices of the bruxism mouth guard device.

In still a further embodiment, the bruxism mouth guard device further comprises one or more sensor cover members configured to be inserted into respective ones of the one or more recesses in the mouth guard body portion in order to cover one or more respective portions of the one or more pressure sensing devices.

In yet a further embodiment, the power source of the bruxism mouth guard device comprises one or more batteries, the recharging unit configured to wirelessly recharge the one or more batteries by means of inductive charging.

It is to be understood that the foregoing general description and the following detailed description of the present invention are merely exemplary and explanatory in nature.

As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 10 is a rear elevational view of the bruxism mouth guard device of FIG. 9a;

FIG. 12 is a side elevational view of the bruxism mouth guard device of FIG. 9a;

Throughout the figures, the same parts are always denoted using the same reference characters so that, as a general rule, they will only be described once.

DETAILED DESCRIPTION OF EMBODIMENTS OF THE INVENTION

Figure 7:
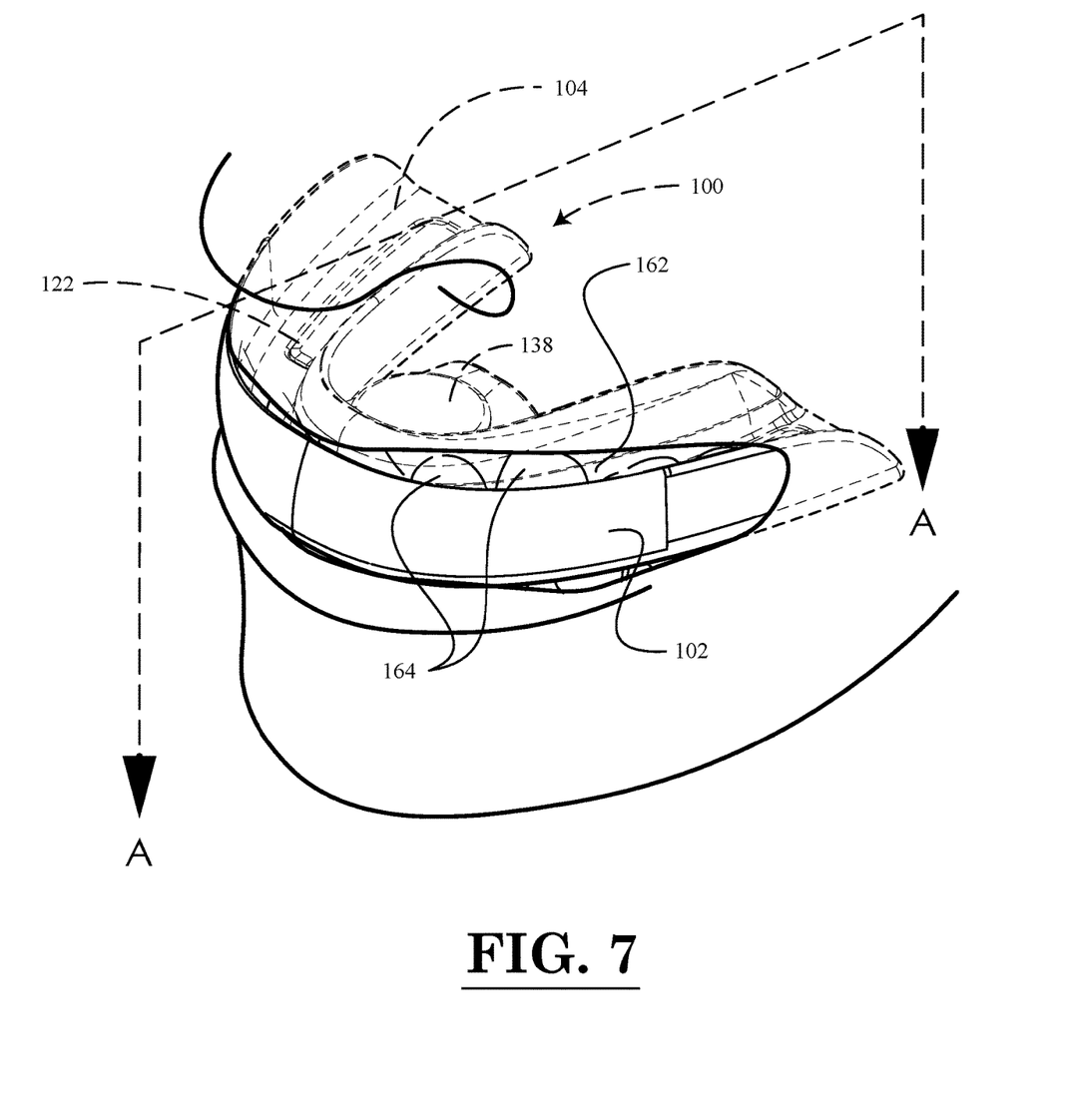
FIG. 7 is a perspective view illustrating the bruxism mouth guard device of FIG. 1 being disposed in the mouth of a user.
Figure 8:
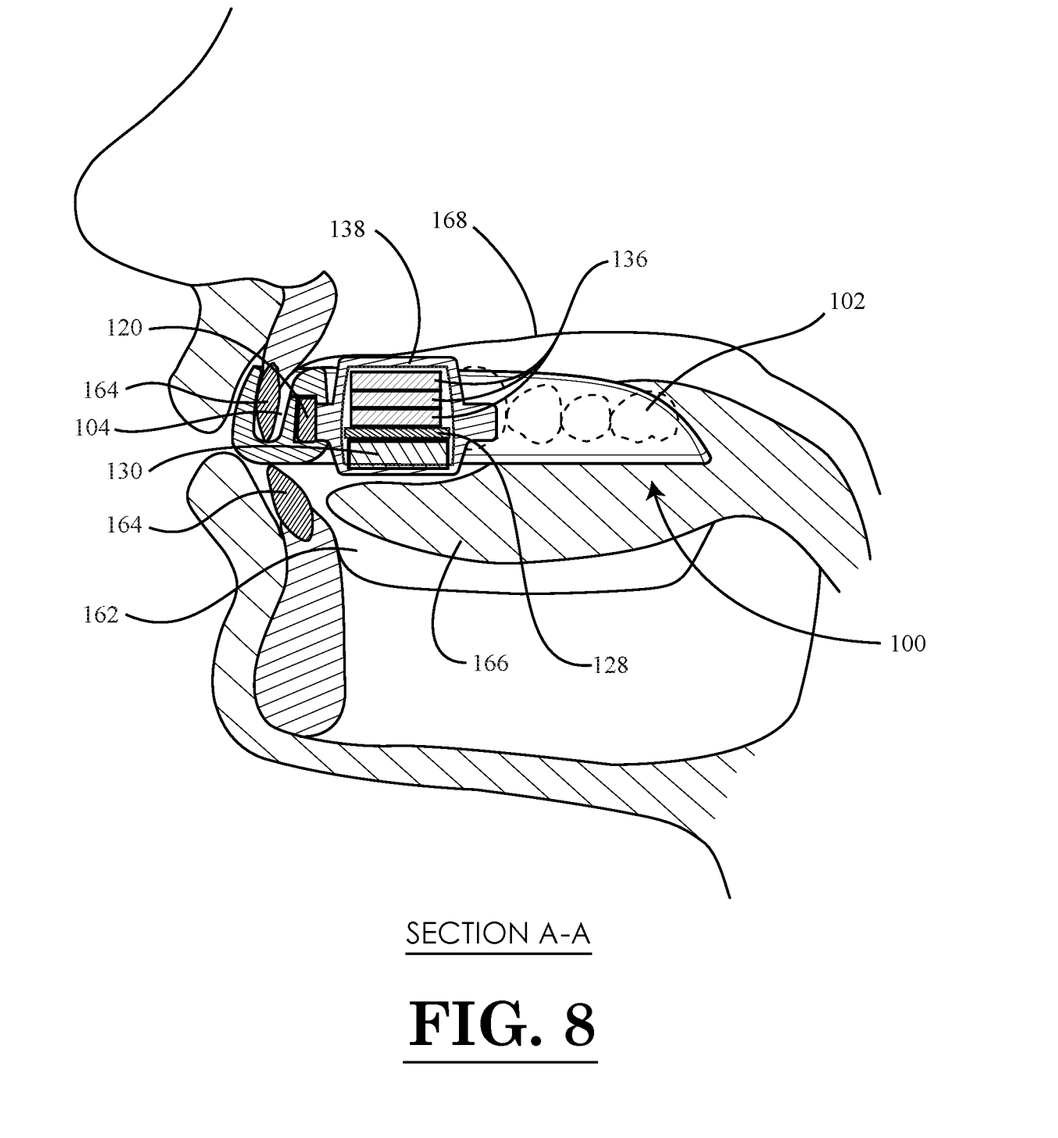
FIG. 8 is a sectional view of the bruxism mouth guard device disposed in the mouth of the user, wherein the section is generally cut along the sagittal cutting-plane line A-A in FIG. 7.

A first illustrative embodiment of a bruxism mouth guard device is seen generally at 100 in FIGS. 1, 2, 4a, 7-9a, and 10-13. In the illustrative embodiment, referring initially to FIGS. 1, 2, and 4a, the bruxism mouth guard device 100 generally comprises (i) a mouth guard body portion 102, the mouth guard body portion 102 comprising a channel 104 formed therein that is configured to receive one or more teeth of a user (as shown in FIGS. 7 and 8); (ii) a pair of pressure sensing devices 124 disposed in the mouth guard body portion 102, the pair of pressure sensing devices 124 configured to sense a grinding or clenching of the teeth 164 of the user; (iii) a vibration device 130 disposed on the mouth guard body portion 102, the vibration device 130 configured to vibrate one or more portions of the mouth 162 of the user (see FIG. 8); and (iv) a control device operatively coupled to the pair of pressure sensing devices 124 and the vibration device 130, the control device 128 configured to activate the vibration device 130 so as to vibrate the one or more portions of the mouth 162 of the user when one or more of the pressure sensing devices 124 sense the grinding or clenching of the teeth 164 by the user in order to prevent the grinding or clenching of the teeth 164 by the user. Advantageously, the bruxism mouth guard device 100 utilizes a two-part construction with a sensing and vibration assembly 112 (see FIG. 2) that is separable from the mouth guard body portion 102 so that the mouth guard body portion 102 may be easily cleaned without damaging the electronics in the sensing and vibration assembly 112.

Figure 1:
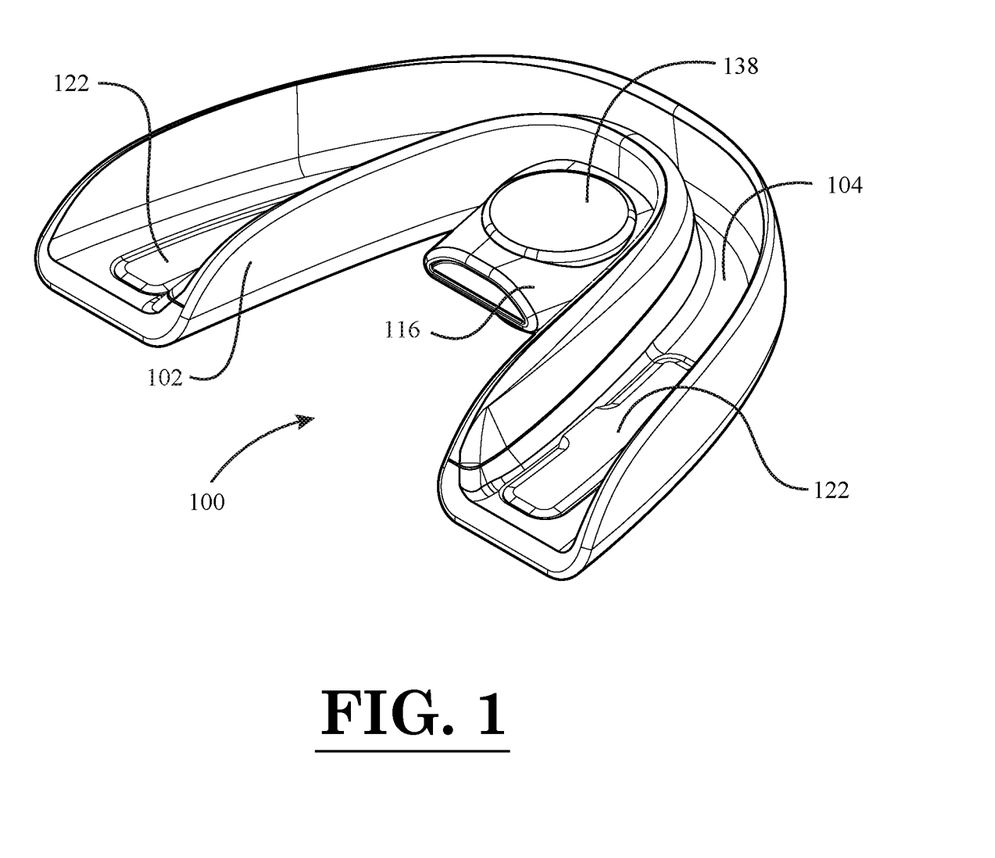
FIG. 1 is a perspective view of a bruxism mouth guard device according to a first embodiment of the invention.
Figures 2, 3:
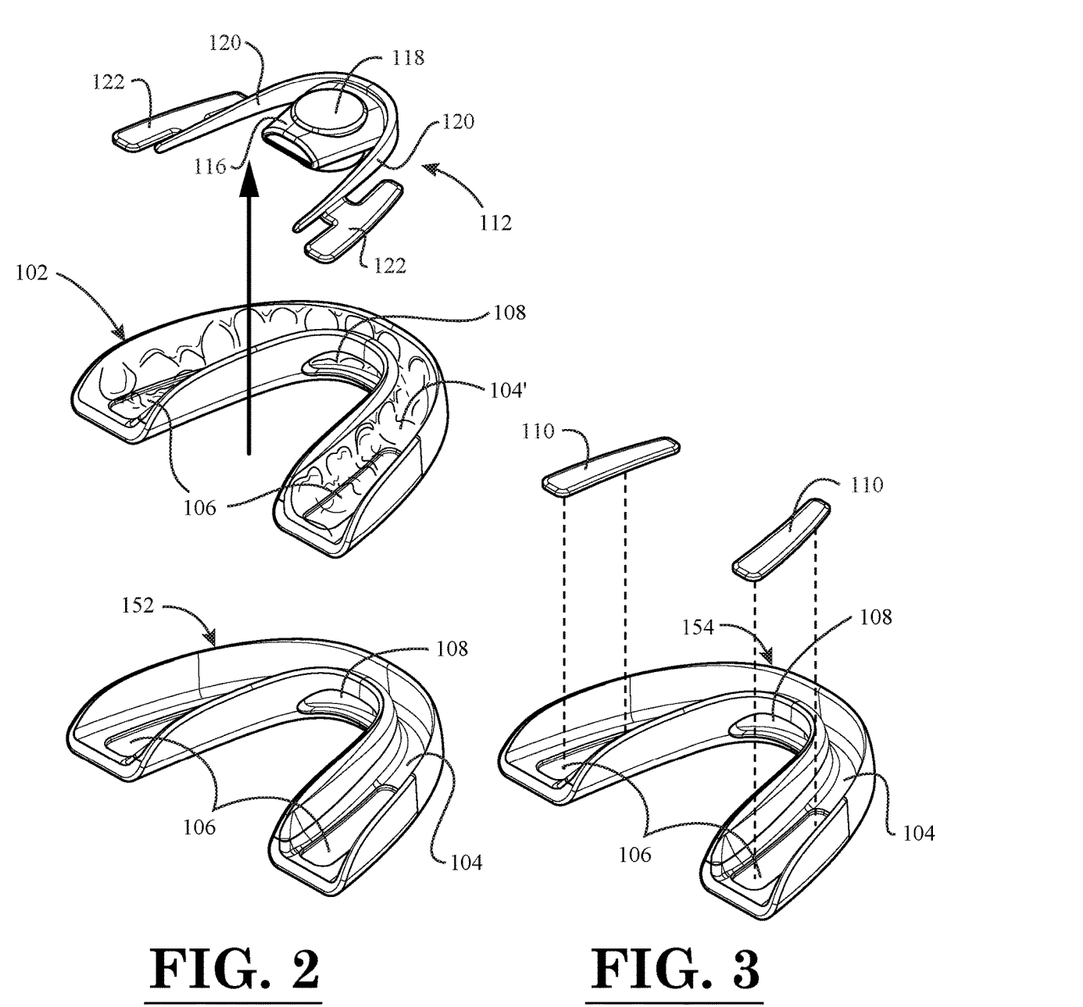
FIG. 2 is a partially exploded perspective view of the bruxism mouth guard device of FIG. 1 together with an extra mouth guard provided as part of a mouth guard kit.
FIG. 3 is a perspective view of another extra mouth guard of the bruxism mouth guard device of FIG. 1, wherein sensor insert members are shown exploded from the remainder of the mouth guard body portion.
Figure 6:
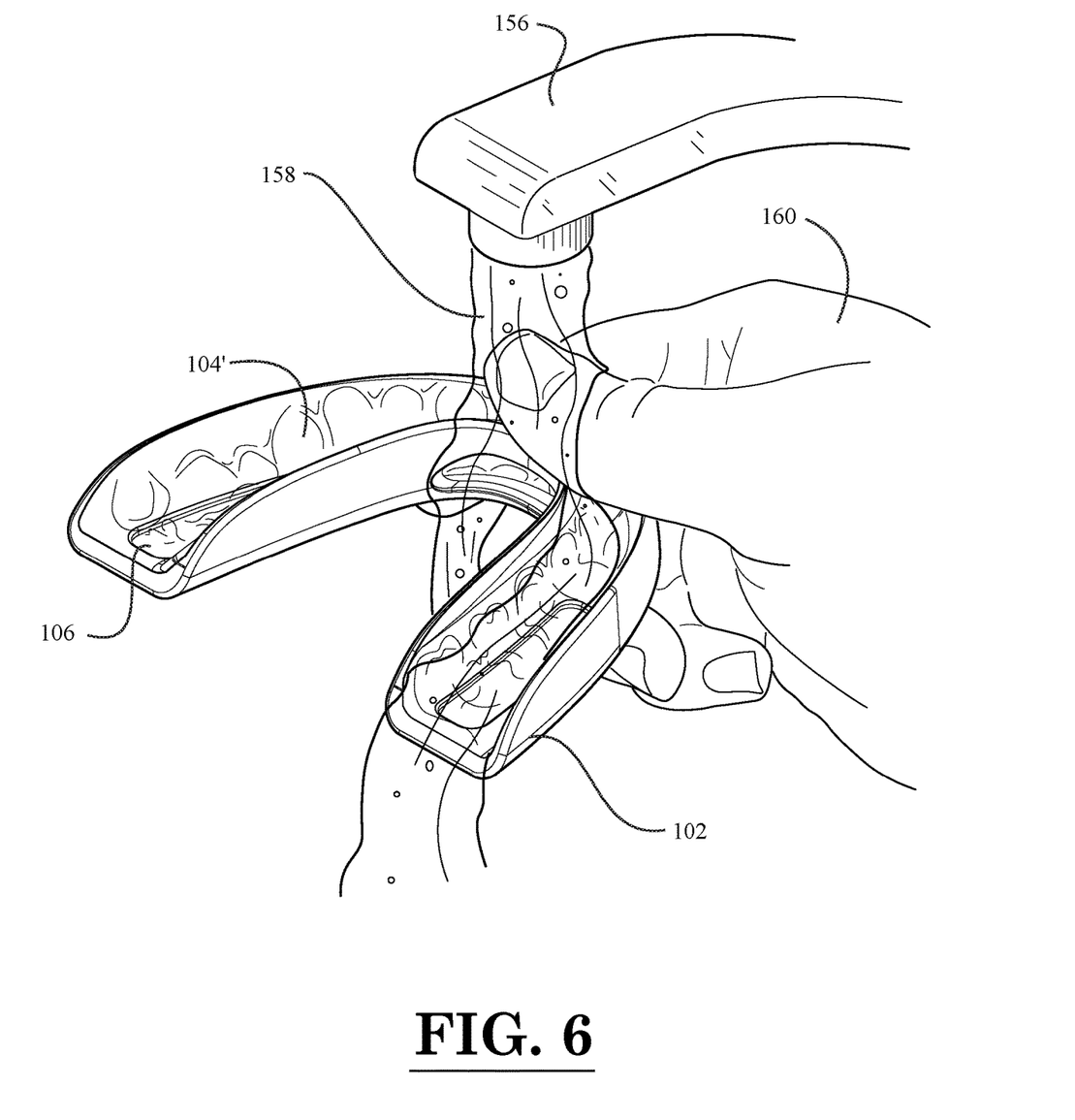
FIG. 6 is a perspective view illustrating the mouth guard body portion of the bruxism mouth guard device of FIG. 1 being rinsed with water so as to clean the mouth guard body portion after use.

Now, with reference primarily to FIGS. 2 and 4a, the sensing and vibration assembly 112 of the bruxism mouth guard device 100 will be described. As best shown in the exploded view of FIG. 4a, the pair of pressure sensing devices 124 and the vibration device 130 are each part of the sensing and vibration assembly 112. In the illustrative embodiment, the sensing and vibration assembly 112 is removable from the mouth guard body portion 102 so as to enable the mouth guard body portion 102 to be cleaned separately from the sensing and vibration assembly 112. For example, as shown in FIG. 6, the mouth guard body portion 102 of the bruxism mouth guard device 100 is capable of being washed separately from the electrical components of the sensing and vibration assembly 112 so that the electrical components are not damaged by the water used to clean the mouth guard body portion 102. After removing the sensing and vibration assembly 112 from the mouth guard body portion 102, it can be seen that the mouth guard body portion 102 may be rinsed with water 158 from a faucet 156 in order to clean the mouth guard body portion 102 between uses thereof. In FIG. 6, a user is holding the mouth guard body portion 102 with his or her hand 160 while the mouth guard body portion 102 is being cleaned with fresh water 158 from the faucet 156. The channel 104' of the mouth guard body portion 102 in FIG. 6 contains teeth indentations imprinted on the bottom and side surfaces thereof created by the teeth of the user.

Figure 4A:
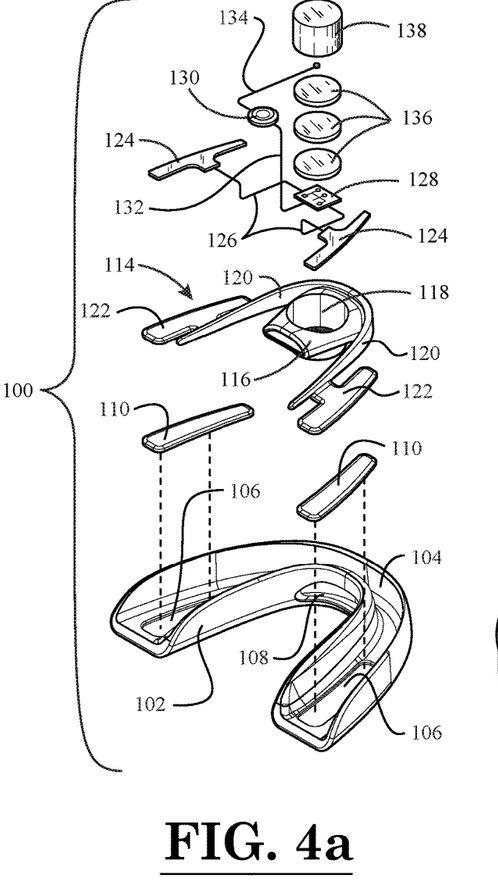
FIG. 4a is an exploded perspective view of the bruxism mouth guard device of FIG. 1.

Referring again to the exploded view of FIG. 4a, it can be seen that the sensing and vibration assembly 112 further comprises a power source configured to provide power for the pair of pressure sensing devices 124, the vibration device 130, and the control device 128. In the illustrative embodiment, the power source of the sensing and vibration assembly 112 comprises a plurality of button cell batteries 136 (e.g., three (3) lithium button cell batteries). Also, in the illustrative embodiment, the pair of pressure sensing devices 124 are in the form of piezoelectric sensors (e.g., piezoelectric pressure sensor strips) configured to sense a compression force exerted thereon by the grinding or clenching of the teeth 164 by the user. The vibration device 130 may be in the form of mini vibrating disk configured to impart a tactile sensation on a portion of the mouth of the user.

Further, in the illustrative embodiment, the control device 128 of the sensing and vibration assembly 112 is in the form of a printed circuit board (PCB) that is operatively coupled to the pair of pressure sensing devices 124 and the vibration device 130 (see FIG. 4a). In particular, as shown in FIG. 4a, each of the pressure sensing devices 124 is electrically connected to the control device 128 by respective electrical wires 126. Similarly, the vibration device 130 is electrically connected to the control device 128 by an electrical wire 132. The vibration device 130 also contains an additional electrical wire 134 connected thereto for electrically coupling the vibration device 130 to the plurality of batteries 136. The PCB control device 128 is configured to activate the vibration device 130 so as to vibrate one or more portions of the mouth 162 of the user (e.g., the roof 168 of the mouth and the tongue 166 of the user—see FIG. 8) when one or more of the pressure sensing devices 124 sense the grinding or clenching of one or more teeth 164 of the user above a predetermined threshold value (e.g., above a predetermined pressure value in pound-force per square inch (lbf/sq. in. or psi) or Newtons per square meter ($N/m^2$)). For example, the threshold range for bruxism detection by the pressure sensing devices 124 may be adjustable in the range between approximately 50 lbf/sq. in. (344,738 $N/m^2$) and approximately 80 lbf/sq. in. (551,581 $N/m^2$). Thus, as one such example, if the pressure measured by the pressure sensing devices 124 exceeds 50 lbf/sq. in., the PCB control device 128 may be configured to activate the vibration device 130. The PCB control device 128 controls the operation of the pressure sensing devices 124 in accordance with a teeth grinding level (i.e., a pressure setting) that is input by the user on a portable digital device 170 (see FIG. 14), which will be described hereinafter.

Next, with reference again to FIGS. 2 and 4a, the housing 114 of the sensing and vibration assembly 112 will be explained. As shown in these figures, the housing 114 of the sensing and vibration assembly 112 includes a central housing portion 116 containing the vibration device 130, the control device 128, and the power source 136. The housing 114 further includes a peripheral housing portion connected to the central housing portion 116 for containing the pressure sensing devices 124 and the electrical wiring extending thereto. Specifically, the peripheral housing portion of the housing 114 includes oppositely disposed sensor housing portions 122 containing the pressure sensing devices 124 and a horseshoe-shaped peripheral connector portion 120 that houses the electrical wiring 126 coupling the pressure sensing devices 124 to the PCB control device 128. The horseshoe-shaped peripheral connector portion 120 of the housing 114 attaches the oppositely disposed sensor housing portions 122 to the centrally disposed housing portion 116. In FIG. 4a, it can be seen that the central housing portion 116 comprises a cylindrical recess 118 disposed therethrough for accommodating the electrical components 128, 130, 136 within the central housing portion 116. The electrical components 128, 130, 136 are enclosed within the central housing portion 116 by means of a cylindrical cover member 138 is received within the recess 118 of the central housing portion 116 (i.e., the cylindrical cover member 138 together with the bounding walls of the recess 118 define an enclosed chamber for holding electrical components 128, 130, 136).

With combined reference to FIGS. 2, 3, and 4a of the illustrated embodiment, the features of the mouth guard body portion 102 of the bruxism mouth guard device 100 will be described. As shown in these figures, the posterior wall of the front portion of the mouth guard body portion 102 comprises an aperture 108 disposed therethrough that is configured to accommodate the tongue-like central housing portion 116 passing therethrough (see FIG. 1). In addition, as shown in FIGS. 2, 3, and 4a, the mouth guard body portion 102 further comprises a pair of sensor recesses 106 for receiving respective ones of the pair of pressure sensing devices 124 of the bruxism mouth guard device 100. In the illustrative embodiment, each recess 106 is disposed within the top surface of the bottom wall of the mouth guard body portion 102 on a respective opposite side of the mouth guard body portion 102. The sensor recesses 106 are located on the posterior portion of the mouth guard body portion 102 so as to accommodate the pressure sensing devices 124 in a location proximate to the molar teeth of the user. Also, in the illustrative embodiment, the bruxism mouth guard device 100 further comprises a pair of sensor cover members 110 configured to be inserted into respective ones of the sensor recesses 106 in the mouth guard body portion 102 in order to cover respective ones of the pressure sensing devices 124 (refer to FIGS. 3 and 4a). The sensor cover members 110 fill in the gaps between the recessed pressure sensing devices 124 and the top surface of the bottom wall of the guard channel 104 so that the bottom wall of the guard channel 104 is essentially a continuous flat surface. Advantageously, the sensor cover members 110 help to ensure that the teeth 164 of the user activate the pressure sensing devices 124 when clenched because the sensor cover members 110 prevent the teeth 164 from merely extending into a void above the pressure sensing devices 124. In some embodiments, rather than providing the sensor cover insert members 110, the thicknesses of the sensor housing portions 122 may be increased such that the top surfaces of the sensor housing portions 122 lie generally flush with the top surface of the bottom wall of the guard channel 104.

In the illustrative embodiment, the mouth guard body portion 102 may be formed from an elastically deformable polymeric material, such as silicone. As such, the mouth guard body portion 102 is capable of readily conforming to the particular geometry of the user's mouth 162.

Also, in one or more embodiments, a plurality of mouth guard body portions 102 may be provided with a single sensing and vibration assembly 112 as part of a bruxism mouth guard kit. For example, as shown in FIGS. 2 and 3, an exemplary kit may be provided with a first mouth guard body portion 102 and two extra mouth guard body portions 152, 154. Advantageously, by providing multiple mouth guard body portions 102, 152, 154 within a kit, a user is able to simply discard one of the mouth guard body portions when it becomes worn out, and then continue using the sensing and vibration assembly 112 with one of the other two mouth guard body portions provided in the kit.

As shown in the sectional view of FIG. 8, in the illustrative embodiment, the central housing portion 116 and the cover member 138 of the sensing and vibration assembly 112 is configured to extend between a tongue 166 of the user and a roof 168 of the mouth 162 of the user such that the vibration device 130 is capable of vibrating both the tongue 166 of the user and the roof 168 of the mouth 162 of the user. As such, by providing a tactile sensation to both the tongue 166 and the roof 168 of the mouth 162 of the user, the bruxism mouth guard device 100 is able to effectively alert the user when he or she is grinding or clenching his or her teeth during sleep. In the illustrative embodiment, the vibration device 130 emits a vibration that is sufficient to alert the brain of the user so as to result in the ceasing of the grinding or clenching of his or her teeth, but it does not wake up the user during sleep.

Figure 11:
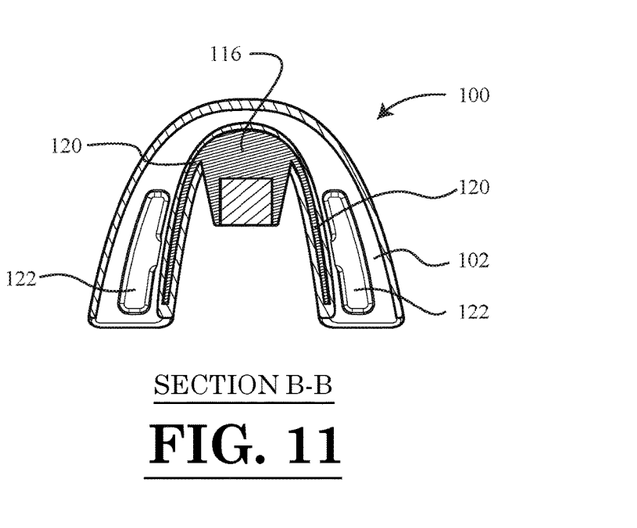
FIG. 11 is a longitudinal sectional view of the bruxism mouth guard device of FIG. 9a, wherein the section is generally cut along the cutting-plane line B-B in FIG. 10.
Figure 12:
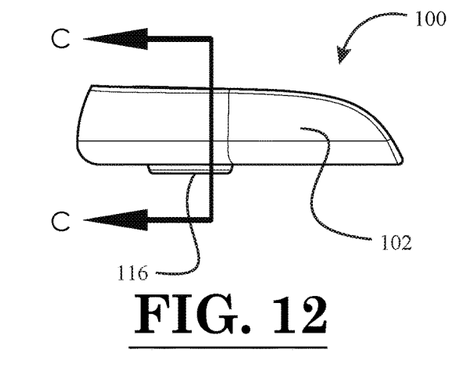
Figure 13:
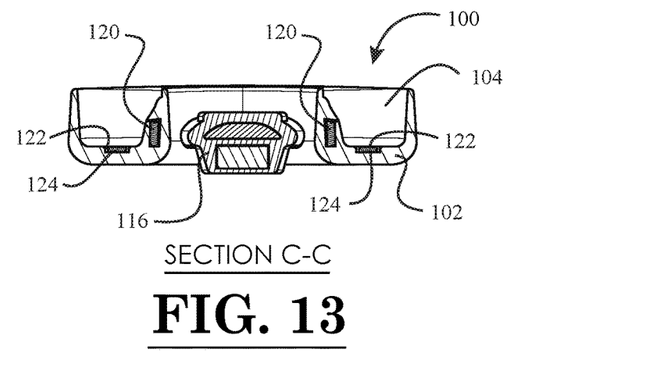
FIG. 13 is a transverse sectional view of the bruxism mouth guard device of FIG. 9a, wherein the section is generally cut along the cutting-plane line C-C in FIG. 12.

Turning to the sectional views of FIGS. 11 and 13, it can be seen that the peripheral housing portion of the sensing and vibration assembly 112 is configured to be interiorly disposed within the mouth guard body portion 102. More particularly, as shown in these figures, the horseshoe-shaped peripheral connector portion 120 of the sensing and vibration assembly housing 114 is configured to be disposed within a cavity of the inner sidewall of the mouth guard body portion 102. In the illustrated embodiment, a slit is formed in the inner sidewall of the mouth guard body portion 102 that extends into the sidewall cavity so as to allow the top portion of the inner sidewall to be elastically deformed by a user, and the peripheral connector portion 120 of the sensing and vibration assembly housing 114 to be inserted into the sidewall cavity. When the sensing and vibration assembly 112 is being attached to the mouth guard body portion 102, the tongue-like central housing portion 116 is first passed through the aperture 108 in the posterior front wall of the mouth guard body portion 102, then the horseshoe-shaped peripheral connector portion 120 of the sensing and vibration assembly housing 114 is inserted into the peripheral inner sidewall cavity of the mouth guard body portion 102 by the user "peeling back" the top portion of the elastically deformable mouth guard body portion 102.

Figure 4B:
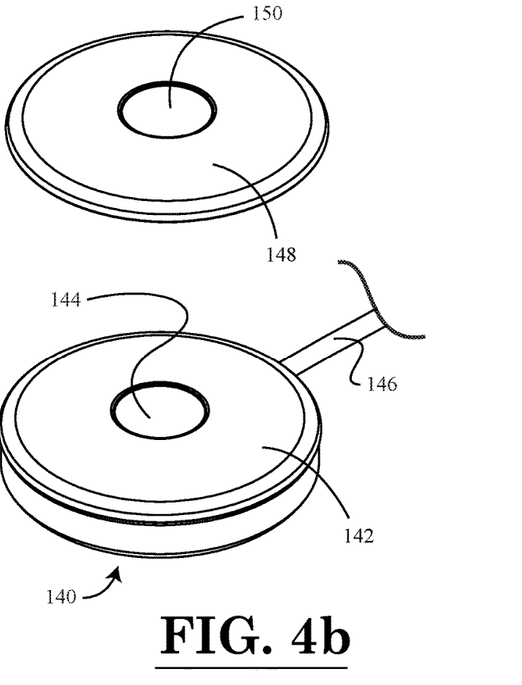
FIG. 4b is a perspective view of a recharging unit for recharging the power source of the bruxism mouth guard device of FIG. 1.

Now, referring to FIGS. 4b and 5, the battery charging unit 140 that is used for recharging the batteries 136 of the bruxism mouth guard device 100 will be described. In one or more embodiments, the bruxism mouth guard device 100 may be provided as part of a bruxism mouth guard system, which also includes the battery charging unit 140 depicted in FIGS. 4b and 5. Initially, as shown in FIG. 4b, the battery charging unit 140 comprises a charger body portion 142 with a centrally disposed charging recess 144, and a power cord 146 for connecting the battery charging unit 140 to a power source (e.g., a 120-volt power receptacle in a dwelling). As shown in FIG. 4b, the battery charging unit 140 may also be provided with a removable plastic shield member 148 that is configured to fit over the top surface of the battery charging unit 140 so as to protect the top surface of the battery charging unit 140 when the sensing and vibration assembly housing 114 is disposed thereon. The plastic shield member 148 comprises a centrally disposed aperture 150 formed therethrough that aligns with the centrally disposed charging recess 144 of the charger body portion 142. In the illustrative embodiment, the battery charging unit 140 is in the form of an induction charging unit that is configured to wirelessly recharge the batteries 136 by means of inductive charging. As such, the battery charging unit 140 does not require the batteries 136 to be removed from the sensing and vibration assembly housing 114 in order to undergo charging.

Figure 5:
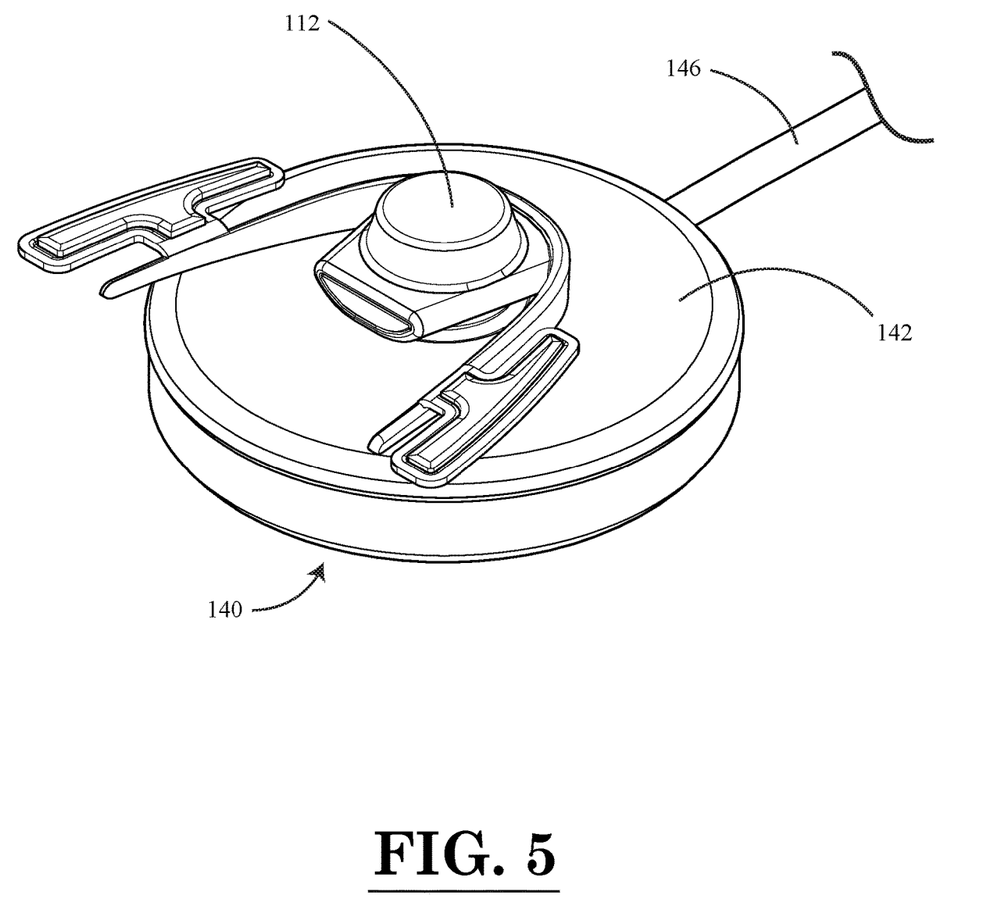
FIG. 5 is another perspective view illustrating the sensing and vibration assembly of the bruxism mouth guard device of FIG. 1 disposed on the recharging unit so that the power source of the sensing and vibration assembly is capable of being recharged using the recharging unit.

FIG. 5 illustrates the sensing and vibration assembly 112 of the bruxism mouth guard device 100 disposed on the battery recharging unit 140 so that the batteries 136 of the sensing and vibration assembly 112 are capable of being recharged using the recharging unit 140. As shown in FIG. 5, during the charging of the batteries 136 of the bruxism mouth guard device 100, the sensing and vibration assembly 112 is configured to be disposed on the top of the recharging unit 140 without being attached to the mouth guard body portion 102. Thus, in order to charge the batteries 136 of the bruxism mouth guard device 100, the sensing and vibration assembly 112 is first removed from the mouth guard body portion 102, and then it is placed on the top of the battery charging unit 140 in the manner illustrated in FIG. 5. When disposed on the battery charging unit 140, a bottom cylindrical portion of the central housing portion 116 of the sensing and vibration assembly 112 of the bruxism mouth guard device 100 is configured to be received within the recess 144 on the top of the recharging unit 140. Once the sensing and vibration assembly 112 is disposed in its charging position on the top of the battery charging unit 140 (FIG. 5), the batteries 136 of the sensing and vibration assembly 112 are recharged by means of inductive charging.

Figure 9A:
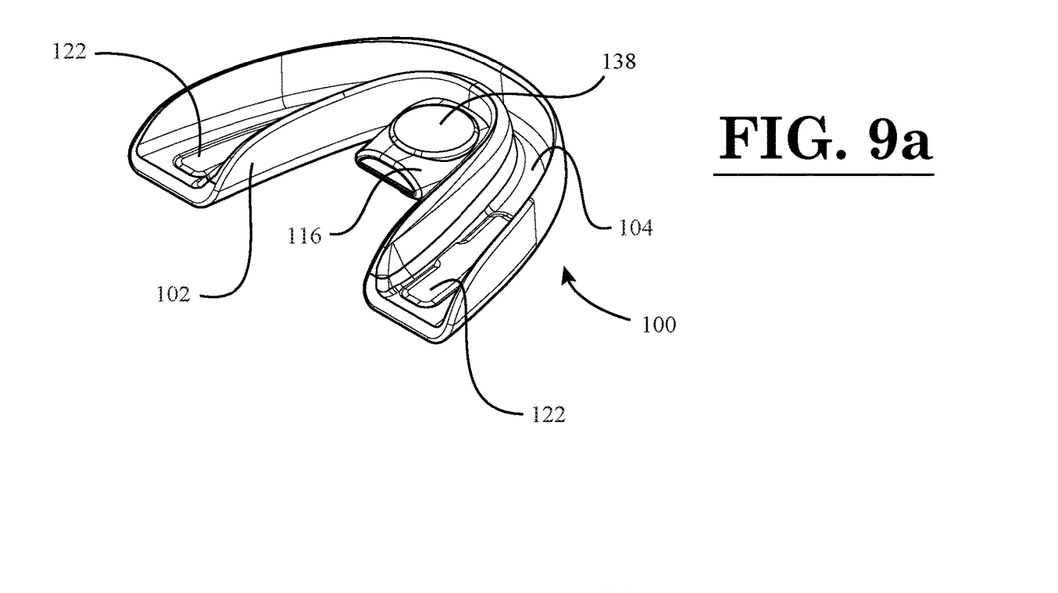
FIG. 9a is another perspective view of the bruxism mouth guard device of FIG. 1.
Figure 9B:
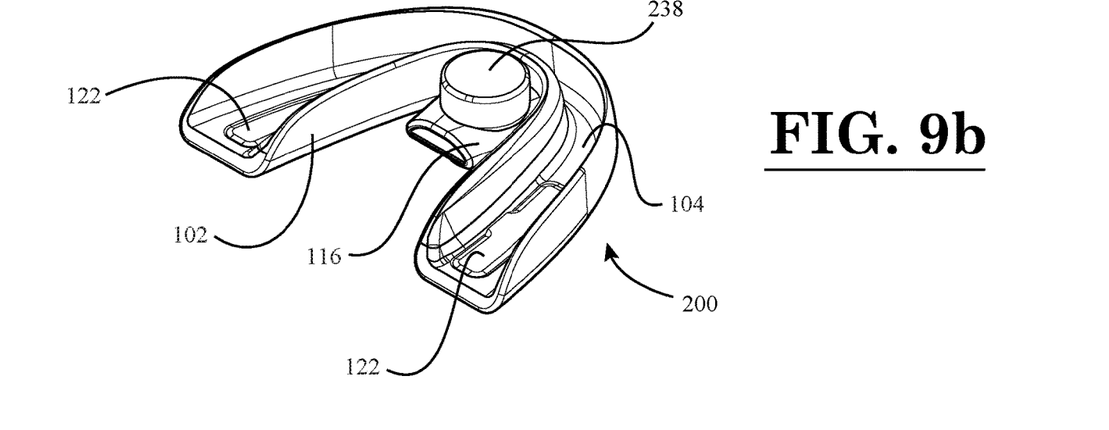
FIG. 9b is a perspective view of a bruxism mouth guard device according to a second embodiment of the invention.
Figure 10:
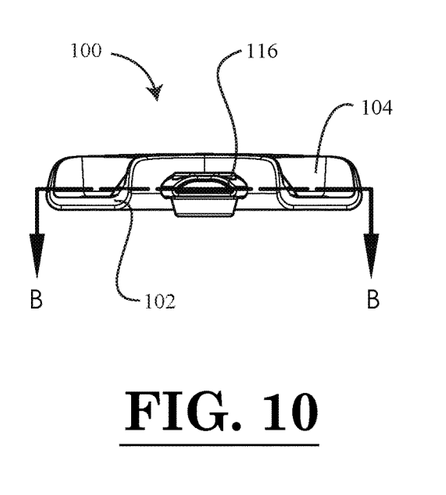

A second illustrative embodiment of the bruxism mouth guard device is seen generally at 200 in FIG. 9b. Referring to this figure, it can be seen that, in most respects, the second illustrative embodiment is the same as the first illustrative embodiment. Moreover, nearly all of the elements are common to both such embodiments. For the sake of brevity, the elements that the second embodiment of the bruxism mouth guard device has in common with the first embodiment will not be discussed because these components have already been described above.

Referring to FIG. 9b, it can be seen that the bruxism mouth guard device 200 is generally the same as the bruxism mouth guard device 100 described above, except that the cylindrical cover member 238 of the sensing and vibration assembly housing 114 has been extended to ensure that it contacts the palate or roof 168 of the user's mouth 162. The extended cylindrical cover member 238 of the bruxism mouth guard device 200 ensures that the vibrations generated by the vibration device 130 will be imparted on both the tongue 166 of the user and the palate 168 of the user, particularly in users having a taller mouth cavity.

Figure 14:
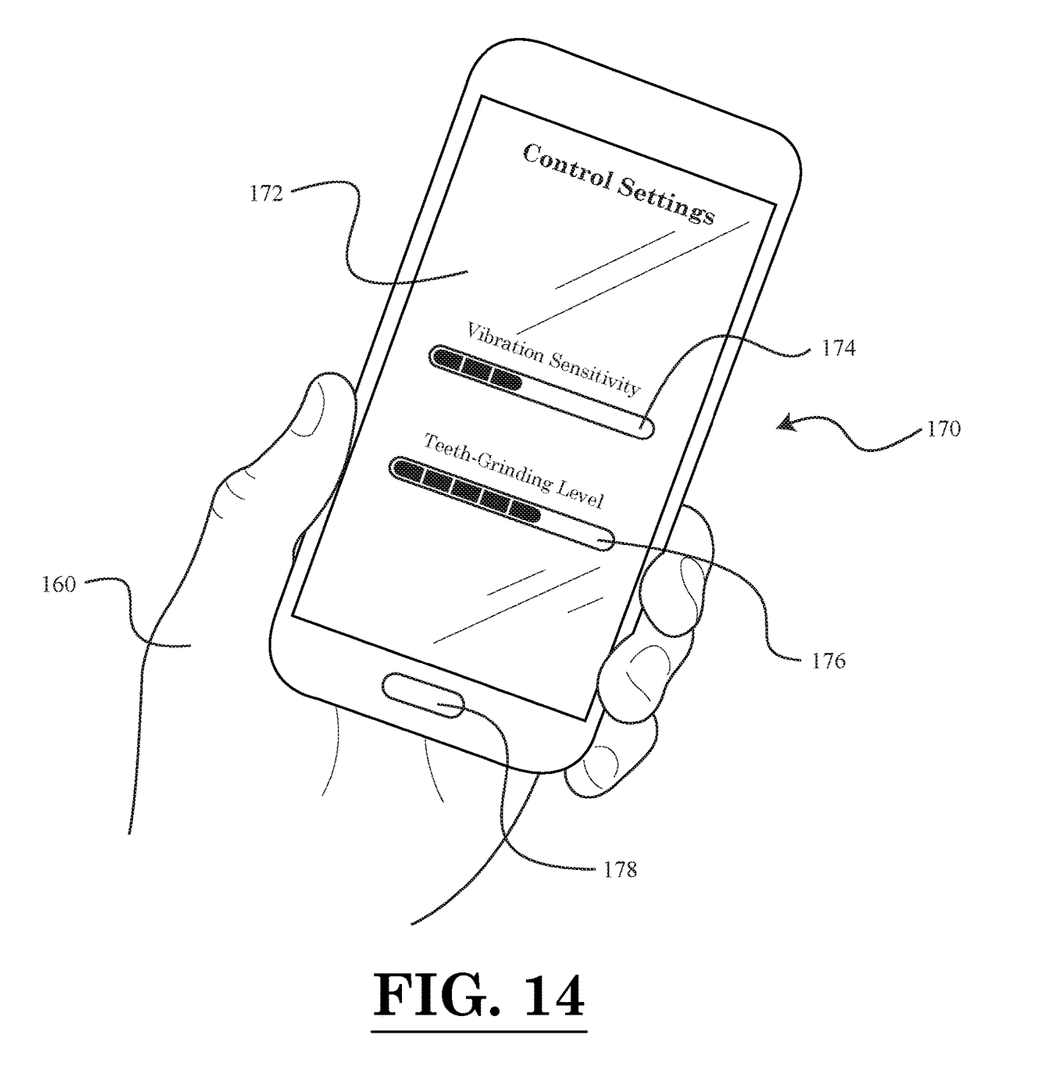
FIG. 14 is a perspective view of a portable digital device with a control screen for controlling the operation of the bruxism mouth guard device described herein.

In the illustrative embodiments, the bruxism mouth guard device 100, 200 further comprises a wireless data interface (e.g., a wireless transmission component) for wirelessly communicating with a portable digital device (e.g., a cellular smartphone 170—see FIG. 14). In particular, the wireless data interface of the bruxism mouth guard device 100, 200 may be configured to wirelessly communicate with the portable digital device 170 by means of a wireless personal area network (e.g., Bluetooth® low energy or Bluetooth® LE) or a wireless local area network (e.g., Wi-Fi®).

In the illustrative embodiment of FIG. 14, the portable digital device 170 is in the form of a smartphone or a smart cellular phone with a mode/home button 178 that is configured to be held in the hand 160 of the user. Also, in the illustrative embodiment, an application software program for controlling the operation of the bruxism mouth guard device 100, 200 is loaded on, and executed by portable digital device 170 so that the user is able to easily modify the operational parameters of the device 100, 200. As shown in FIG. 14, the illustrative portable digital device 170 comprises a touchscreen user interface that enables a user to manipulate visual objects on the screen of the smart digital device 170 using his or her fingers. The portable digital device 170 is specially programmed so as to enable the user to adjust the operational settings of the bruxism mouth guard device 100, 200 using the touchscreen user interface of the portable digital device 170. An exemplary control screen 172 for the bruxism mouth guard device 100, 200 is illustrated in FIG. 14. In FIG. 14, it can be seen that the control screen 172 is provided with adjustable level setting means 174 for the vibration sensitivity of the vibration device 130 of the bruxism mouth guard device 100, 200 and adjustable level setting means 176 for the teeth-grinding detection level of the pressure sensing devices 124 of the bruxism mouth guard device 100, 200 (e.g., a grinding level adjustable between 50 lbf/sq. in. and 80 lbf/sq. in.). In addition to allowing the user to adjust the speed of the vibrations produced by the vibration device 130 and the pressure level setting for the pressure sensing devices 124, the application software program for controlling the bruxism mouth guard device 100, 200 that is executed by the portable digital device 170 may also track the grinding of the user's teeth over time so that the user is able to assess whether the bruxism condition is improving over time. The application software program for controlling the bruxism mouth guard device 100, 200 may monitor the daily use of the device 100, 200 (e.g., track trends in the grinding pressure) so that the grinding level may be modified manually or automatically to avoid false alerts and detect more bruxism events at the beginnings thereof. Also, to avoid false alerts, the application software program may require the threshold grinding level to occur for a predetermined period of time (e.g., 1.0 second or more) before resulting in an alarm trip condition that activates the vibration device 130, thereby preventing momentary jaw movements from creating undesirable false alerts. Further, the application software program may take into account other factors, such as sleep status (e.g., as determined by an accelerometer in the portable digital device 170), when determining whether or not to trigger the vibration device 130. Advantageously, because all of the operational settings of the bruxism mouth guard device 100, 200 are capable of being adjusted using the touchscreen user interface of the portable digital device 170, there is no need for any display or control panel to be provided on the bruxism mouth guard device 100, 200 itself.

While the portable digital device 170 for the controlling the operational settings of the bruxism mouth guard device 100, 200 is in the form of a smartphone in the illustrative embodiment, it is to be understood that, in other embodiments, the portable digital device may alternatively being in the form of: (i) a tablet device, (ii) a laptop computing device, (iii) a palmtop computing device, or (iv) a desktop computing device.

It is readily apparent that the aforedescribed bruxism mouth guard device 100, 200 and the bruxism mouth guard system including the same offers numerous advantages. First, the bruxism mouth guard device 100, 200 is configured to prevent the grinding or clenching of teeth of a user by providing a tactile sensation in the mouth of the user when the grinding or clenching of teeth is sensed. Secondly, the aforedescribed bruxism mouth guard device 100, 200 is capable of continually alerting a user of teeth grinding or clenching during sleep so that the frequency of the teeth grinding or clenching may eventually decrease over time. Finally, the bruxism mouth guard system described herein enables the mouth guard portion of the device to be easily cleaned after use, and allows the power source of the device 100, 200 to be easily recharged between uses of the device.

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A bruxism mouth guard system, comprising:
a bruxism mouth guard device configured to worn inside a mouth of a user, said bruxism mouth guard device including:
a mouth guard body portion, said mouth guard body portion comprising a channel formed therein that is configured to receive one or more teeth of said user, and said mouth guard body portion being U-shaped with a central void bounded by an interior peripheral wall of said mouth guard body portion, said interior peripheral wall of said mouth guard body portion comprising an aperture at the anterior apex of said mouth guard body portion that is in communication with an internal cavity of said mouth guard body portion;
one or more pressure sensing devices in or on said mouth guard body portion, said one or more pressure sensing devices configured to sense a grinding or clenching of said one or more teeth of said user;
a vibration device in or on said mouth guard body portion, said vibration device configured to vibrate one or more portions of said mouth of said user;
a control device operatively coupled to said one or more pressure sensing devices and said vibration device, said control device configured to activate said vibration device so as to vibrate said one or more portions of said mouth of said user when said one or more pressure sensing devices sense the grinding or clenching of said one or more teeth by said user in order to prevent the grinding or clenching of said one or more teeth by said user; and
a power source configured to provide power for said one or more pressure sensing devices, said vibration device, and said control device; and
a recharging unit configured to recharge said power source of said bruxism mouth guard device;
wherein said one or more pressure sensing devices and said vibration device of said bruxism mouth guard device are each part of a sensing and vibration assembly, said sensing and vibration assembly of said bruxism mouth guard device comprising a central housing portion containing said vibration device, said control device, and said power source; and
said aperture in said interior peripheral wall of said mouth guard body portion configured to accommodate a portion of said central housing portion passing therethrough into said central void of said mouth guard body portion.

2. The bruxism mouth guard system according to claim 1, wherein said sensing and vibration assembly is removable from said mouth guard body portion so as to enable said mouth guard body portion to be cleaned separately from said sensing and vibration assembly.

3. The bruxism mouth guard system according to claim 2, wherein
said sensing and vibration assembly additionally comprises a peripheral housing portion containing said one or more pressure sensing devices.

4. The bruxism mouth guard system according to claim 3, wherein said peripheral housing portion of said sensing and vibration assembly of said bruxism mouth guard device is configured to be interiorly disposed within said internal cavity of said mouth guard body portion.

5. The bruxism mouth guard system according to claim 3, wherein said central housing portion of said sensing and vibration assembly of said bruxism mouth guard device is configured to extend between a tongue of said user and a roof of said mouth of said user such that said vibration device is capable of vibrating both said tongue of said user and said roof of said mouth of said user.

6. The bruxism mouth guard system according to claim 3, wherein after said sensing and vibration assembly is removed from said mouth guard body portion, a bottom portion of said central housing portion of said sensing and vibration assembly of said bruxism mouth guard device is configured to be received within a central recess on a top portion of said recharging unit; and wherein, during the charging of said power source of said bruxism mouth guard device, said sensing and vibration assembly is configured to be disposed on said recharging unit without being attached to said mouth guard body portion.

7. The bruxism mouth guard system according to claim 1, wherein said one or more pressure sensing devices of said bruxism mouth guard device are in a form of one or more piezoelectric sensors configured to sense a compression force exerted thereon by the grinding or clenching of said one or more teeth by said user.

8. The bruxism mouth guard system according to claim 1, wherein said control device of said bruxism mouth guard device is in a form of a circuit board that is operatively coupled to said one or more pressure sensing devices and said vibration device, said circuit board configured to activate said vibration device so as to vibrate said one or more portions of said mouth of said user when said one or more pressure sensing devices sense the grinding or clenching of said one or more teeth above a predetermined threshold value.

9. The bruxism mouth guard system according to claim 1, wherein said mouth guard body portion of said bruxism mouth guard device further comprises one or more recesses for receiving respective ones of said one or more pressure sensing devices of said bruxism mouth guard device; and wherein said bruxism mouth guard device further comprises one or more sensor cover members configured to be inserted into respective ones of said one or more recesses in said mouth guard body portion in order to cover one or more respective portions of said one or more pressure sensing devices.

10. The bruxism mouth guard system according to claim 1, wherein said power source of said bruxism mouth guard device comprises one or more batteries, said recharging unit configured to wirelessly recharge said one or more batteries by means of inductive charging.

\* \* \* \* \*